| United States Patent [19] | [11] Patent Number: 4,654,333 |
| Tenoso | [45] Date of Patent: Mar. 31, 1987 |

[54] TREATMENT OF MULTIPLE SCLEROSIS

[75] Inventor: Harold J. Tenoso, Westfield, N.J.

[73] Assignee: Unimed, Inc., Somerville, N.J.

[21] Appl. No.: 829,985

[22] Filed: Feb. 18, 1986

[51] Int. Cl.$^4$ .................... A61K 31/28; A61K 31/555
[52] U.S. Cl. ..................................... 514/184; 514/492
[58] Field of Search ................................ 514/492, 184

Primary Examiner—Stanley J. Friedman
Attorney, Agent, or Firm—Steinberg & Raskin

[57] ABSTRACT

Multiple sclerosis is treated by the administration of azaspirane compounds, either germanium or silicon asaspirane compounds, preferably spirogermanium, most preferably dimethyl, diethyl, dipropyl or dibutyl. The diethyl or dibutyl are the most preferred.

2 Claims, No Drawings

TREATMENT OF MULTIPLE SCLEROSIS

BACKGROUND OF THE INVENTION

Multiple sclerosis (MS) and its variants comprise a distinct group of demyelinating diseases. A typical MS plaque or lesion is an area of grossly visible, well demarcated, demyelinated white matter.

Immunocytochemical studies with monoclonal antibodies against T-cells and other inflammatory components have demonstrated that $T_4+$ (helper, inducer) T-cells are involved in lesion extension.

EAE (experimental allergic encephalomyelitis) is an animal model used to study: (a) immunological effector and suppressor mechanisms in demyelination; (b) acute MS; (c) therapeutic approaches to acute demyelination. This model has been used for several decades as a model for MS. (Raine, C. S.: Biology of Disease, Analysis of Autoimmune Demyelination: Lab. Inv. 50:608-635, 1984, No. 6).

EAE is a condition induced in rats, guinea pigs, and other animals as a model for the study of brain lesions and symptoms resembling MS in humans. (Fleming, J. O.: Animal models of multiple sclerosis. Mayo Clin. Proc. 60:490-492, 1985.) The condition of EAE has proven to be a useful model for the investigation and detection of drugs with possible utility in the treatment of MS patients, acute disseminated encephalomyelitis, and other conditions classified with the primary demyelinating diseases.

SUMMARY OF THE INVENTION

Generally speaking, in accordance with the present invention, it has been discovered that certain specific compounds of U.S. Pat. No. 3,825,546, namely those which contain germanium in the ring, that is the spirogermaniums, particularly the dimethyl, diethyl, dipropyl and dibutyl spirogermaniums including their acid addition salts and bis-quaternary salts, appear to be useful in reducing or preventing the development of EAE lesions in the brain, to suppress the autoimmune reaction asserted to be the ultimate cause of the EAE and MS lesions, and therefore to be useful in the treatment of multiple sclerosis.

It is accordingly a primary object of the present invention to provide for inhibiting the immune reaction against the demyelination and to therefore be useful in the treatment of multiple sclerosis.

It is another object of the present invention to provide for the treatment of multiple sclerosis by the administration of a multiple sclerosis treatment effective amount of a spirogermanium.

Other objects and advantages of the present invention will be apparent from a further reading of the specification and of the appended claims.

The compounds of U.S. Pat. No. 3,825,546, which can be used for the purposes of the present invention are those compounds of the following structural formula:

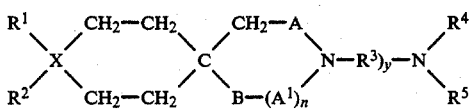

wherein
$R^1$ and $R^2$ are the same or different alkyl groups of 1-4 carbon atoms x = germanium
a and $A^1$ are the same and either

n = 0 or 1
B = $CH_2$ when n is one and B is the same as A when n is zero
$R^3$ = alkylene or alkenylene
y = 2-6 when $R^3$ is alkylene and 3-4 when $R^3$ is alkenylene $R^4$ and $R^5$ are the same or different lower alkyls having 1-4 carbon atoms, lower alkenyls having 3-4 carbons atoms, or cyclicized together form a heterocyclic group selected from morpholino, pyrrolidino, piperazino in which said lower alkyl is attached to a terminal nitrogen atom, as well as acid addition salts and bis-quarternary salts thereof.

The acid addition salts are of course the physiologically compatible acid addition salts, most preferably the dihydrochloride.

The bis-quaternary salts are of course the physiologically compatible bis-quaternary salts including the methiodide and the dimethiodide.

The dimethyl spirogermanium, diethyl spirogermanium, dipropyl spirogermanium and dibutyl spriogermanium which are effective in the treatment of arthritis are:

N-(3-dimethylaminopropyl)-2-aza-8,8-dimethyl-8-germaspiro[4:5] decane;

N-(3-dimethylaminopropyl)-2-aza-8,8-diethyl-8-germaspiro[4:5] decane;

N-(3-dimethylaminopropyl)-2-aza-8,8-dipropyl-8-germaspiro[4:5] decane; and

N-(3-dimethylaminopropyl)-2-aza-8,8-dibutyl-8-germaspiro[4:5] decane.

As indicated previously, the above compounds may be utilized in the form of their acid addition salts or bisquaternary salts. Most preferred are the dihydrochloride salts.

The above compounds may be distributed in any suitable pharmaceutical carrier for administration by injection or for oral administration. Aqueous solution can be prepared of the non-toxic salts which are soluble in water for administration by injection, for examle intravenous administration or intraperitoneal injection, or for oral administration. It is preferred, however, for oral administration to utilize compositions in tablet form, for example tablets with lactose or the like as a carrier.

Although the spirogermaniums can be tolerated in rather high doses without any adverse effects, it having been found safe when given intravenously in doses of 5-80 mg/m² of body surface, and even doses of 120 mg/m² of body surface, much smaller doses can be administered for the purposes of the present invention.

The recommended dose of spirogermanium therapy is 1.5 cc intramuscularly of an aqueous solution of 30 mg/ml (45 mg/dose). Such treatment is given twice weekly for the first six weeks and once weekly thereafter until remission is obtained. This usually requires 3-6 months of treatment.

Oral treatment can be effected by means of capsules containing 200 mg per capsule, beginning with two capsules daily for two weeks and one capsule daily thereafter for six weeks.

The most preferred compound for the purposes of the present invention is the compound: N-(3-dimethylaminopropyl)-2-aza-8,8-diethyl-8-germaspiro[4:5]decane most preferrably in the form of its dihydrochloride. It is this compound which is generally referred to in the following discussion by the abbreviation "SG".

Spirogermanium has been shown to be well adapted for the purpose of the present invention because of the lack of overt toxic effects over prolonged periods of administration of effective doses to animals and humans. Its advantages may be listed as being water soluble; readily absorbed by oral administration; easy acceptance by the gastrointestinal tract; lack of organ toxicity from doses that are adequately immunosuppressant and anti-inflammatory, and that the drug binds to the proteins of the tissues and remains pharmacologically effective over long periods of time.

In experimental investigations on dogs given SG orally for up to a year, there has been no evidence of continuous accumulation of drug in the tissues above that attained at saturation. Importantly, the proteins of the cells combine with the drug and retain it for long periods. The ability of SG to attach to the tissue proteins and formed blood elements allows the maintenance of effective concentrations in the tissues, ensuring continuous action of maintaining immunosuppression. This is an important feature because it obviates continuous administration, increases cost effectiveness by reducing the longterm cost of administration of the drug, and minimizes possible toxicity during prolonge administration.

The drug is used in several ways. If necessary, to attain rapid saturation, it may be initially given intravenously, provided the administration is sufficiently slow. The choice is by oral administration. The drug may be dissolved in water or other liquids, such as fruit juices, milk, etc. Its absorption is not inhibited by food and the dilute solution of the drug ensures that the gastrointestinal tract will accept it. The following formulations are suggested:

(1) Ampuls or vials of 1.0 percent SG in saline for i.v. injection.
(2) Capsules or tablets containing 100 mg SG or other suitable amounts to be used for oral administration.
(3) Capsules containing 100 mg SG or other suitable amounts, the contents of which are to be added to water or other solvents, such as fruit juices or soft drinks, for oral administration.

DESCRIPTION OF THE PREFERRED EMBODIMENTS

The following example is given to further illustrate the present invention. The scope of the invention is not, however, meant to be limited to the specific details of the example.

EXAMPLE

The effectiveness of SG is demonstrated in the EAE model and described in rats treated with Freund's Complete Adjuvant which induces EAE. The data confirms the usefulness of the present invention in the treatment of multiple sclerosis.

Complete Freund's Adjuvant was injected into a hind paw of each of six Lewis rats and kept untreated until the tenth (10) day. Thereafter, each group consisting of one control and one for each dose of SG was injected intraperitoneally with either, saline used as control, or spirogermanium twice daily. The doses varied from 2.5 mg i.p. daily to 5.0 mg twice daily. The animals were subjected daily to a clinical index (CI) assessment on a scale of 0 to 4. The control animals reached a maximum CI of 3.50 on the thirteenth (13) day. The CI returned to 1 to 0 by the sixteenth (16) day from the higher doses. These experiments are being continued and expanded to determine the optimum dose, frequency, and route of administration, and degree of effectiveness.

The SG-treated rats did not exceed a CI of 1, which is considered within normal limits for this experimental model and remained so throughout the eighteen (18) days of observation. Light and electron microscopy showed typical EAE lesions in the brain of the saline-treated rats but virtually none in the brain of the SG-treated rats. This experiment was repeated with similar results. Electron microscopy photographs were made, confirming the results.

While the invention has been described in particular with respect to experiments in rats, it is apparent that variations and modifications of the invention can be made without departing from the spirit or scope thereof.

What is claimed is:

1. Method of treating multiple sclerosis, which comprises administering to a patient suffering from the same a multiple sclerosis treatment effective amount of a spirogermanium selected from the group consisting of N-(3-dimethylaminopropyl)-2-aza-8,8-dimethyl-8-germanspiro[4:5] decane;

N-(3-dimethylaminopropyl)-2-aza-8,8-diethyl-8-germaspiro[4:5] decane;

N-(3-dimethylaminopropyl)-2-aza-8,8-dipropyl-8-germaspiro[4:5] decane; and

N-(3-dimethylaminopropyl)-2-aza-8,8-dibutyl-8-germaspiro[4:5] decane.

2. Method according to claim 1 wherein said compound is N-(3-dimethylaminopropyl)-2-aza-8,8-diethyl-8-germaspiro[4:5] decane.

* * * * *